(12) United States Patent
Keil et al.

(10) Patent No.: US 11,931,592 B2
(45) Date of Patent: Mar. 19, 2024

(54) OUTPUT CIRCUITRY FOR MULTIPLE-THERAPY IMPLANTABLE DEVICES

(71) Applicant: CARDIAC PACEMAKERS, INC., St. Paul, MN (US)

(72) Inventors: Brandon Tyler Keil, Maple Grove, MN (US); William J. Linder, Golden Valley, MN (US); Keith R. Maile, New Brighton, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 461 days.

(21) Appl. No.: 17/173,723

(22) Filed: Feb. 11, 2021

(65) Prior Publication Data

US 2021/0252296 A1 Aug. 19, 2021

Related U.S. Application Data

(60) Provisional application No. 62/976,141, filed on Feb. 13, 2020.

(51) Int. Cl.
*A61N 1/39* (2006.01)

(52) U.S. Cl.
CPC ......... *A61N 1/3956* (2013.01); *A61N 1/3912* (2013.01); *A61N 1/3918* (2013.01); *A61N 1/3981* (2013.01)

(58) Field of Classification Search
CPC .. A61N 1/3956; A61N 1/3912; A61N 1/3918; A61N 1/3981
See application file for complete search history.

(56) References Cited

U.S. PATENT DOCUMENTS

| | | | |
|---|---|---|---|
| 5,507,781 A | 4/1996 | Kroll et al. |
| 5,643,323 A | 7/1997 | Kroll et al. |
| 6,647,292 B1 | 11/2003 | Bardy et al. |
| 6,721,597 B1 | 4/2004 | Bardy et al. |
| 6,754,528 B2 | 6/2004 | Bardy et al. |
| 6,778,860 B2 | 8/2004 | Ostroff et al. |
| 6,865,417 B2 | 3/2005 | Rissmann et al. |
| 6,952,608 B2 | 10/2005 | Ostroff |
| 6,954,670 B2 | 10/2005 | Ostroff |
| 6,968,231 B1 | 11/2005 | Silvian et al. |
| 7,149,575 B2 | 12/2006 | Ostroff et al. |
| 7,330,757 B2 | 2/2008 | Ostroff et al. |
| 7,555,338 B2 | 6/2009 | Ostroff |
| 7,783,340 B2 | 8/2010 | Sanghera et al. |
| 7,860,565 B2 | 12/2010 | Brink |
| 7,877,139 B2 | 1/2011 | Ostroff |
| 8,157,813 B2 | 4/2012 | Ko et al. |
| 8,160,686 B2 | 4/2012 | Allavatam et al. |
| 8,200,341 B2 | 6/2012 | Sanghera et al. |

(Continued)

*Primary Examiner* — Mallika D Fairchild
(74) *Attorney, Agent, or Firm* — Seager, Tufte & Wickhem LLP (57) ABSTRACT

Improved devices, circuits and methods of operation in implantable stimulus systems. An implantable defibrillator may comprise an H-bridge output circuit having low and high sides, with a current controlling circuit coupled to the high side of the H-bridge output circuit and a current monitoring circuit coupled to the low side of the H-bridge output circuit. Alternate current paths to the output of the H-bridge, or to the H-Bridge itself, are used for delivering different therapies to the patient.

9 Claims, 8 Drawing Sheets

(56) References Cited

U.S. PATENT DOCUMENTS

| | | |
|---|---|---|
| 8,209,005 B1 | 6/2012 | Moulder et al. |
| 8,463,392 B2 | 6/2013 | Aghassian |
| 8,473,066 B2 | 6/2013 | Aghassian et al. |
| 8,532,785 B1 | 9/2013 | Crutchfield et al. |
| 8,548,590 B2 | 10/2013 | Aghassian |
| 8,565,878 B2 | 10/2013 | Allavatam et al. |
| 8,620,436 B2 | 12/2013 | Parramon et al. |
| 8,825,157 B2 | 9/2014 | Warren et al. |
| 8,972,005 B2 | 3/2015 | Rasmussen et al. |
| 8,983,599 B2 | 3/2015 | Garrett et al. |
| 9,579,517 B2 | 2/2017 | Meador et al. |
| 9,641,012 B2 | 5/2017 | Cabelka et al. |
| 9,643,025 B2 | 5/2017 | Crutchfield et al. |
| 9,750,950 B2 | 9/2017 | Norton et al. |
| 9,814,889 B2 | 11/2017 | Strommer et al. |
| 9,861,827 B2 | 1/2018 | Cabelka et al. |
| 9,861,828 B2 | 1/2018 | Norton et al. |
| 9,956,442 B2 | 5/2018 | Cooper et al. |
| 10,046,168 B2 | 8/2018 | Nikolski et al. |
| 10,050,700 B2 | 8/2018 | Ludwig et al. |
| 10,080,905 B2 | 9/2018 | Anderson et al. |
| 10,155,119 B2 | 12/2018 | Anderson et al. |
| 10,159,847 B2 | 12/2018 | Rasmussen et al. |
| 10,213,610 B2 | 2/2019 | Maile et al. |
| 10,350,425 B2 | 7/2019 | Nikolski et al. |
| 10,471,267 B2 | 11/2019 | Thompson-Nauman et al. |
| 10,556,118 B2 | 2/2020 | Anderson et al. |
| 2006/0167503 A1 | 7/2006 | Warren et al. |
| 2012/0029335 A1 | 2/2012 | Sudam et al. |
| 2013/0197348 A1* | 8/2013 | Stancer ................ A61N 1/3981 607/6 |
| 2017/0021159 A1 | 1/2017 | Reddy et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2017/0157399 A1* | 6/2017 | Anderson .......... A61N 1/36521 |
| 2018/0036527 A1 | 2/2018 | Reddy et al. |
| 2018/0036547 A1 | 2/2018 | Reddy |
| 2018/0133462 A1 | 5/2018 | Reddy |
| 2021/0252299 A1 | 8/2021 | Keil et al. |
| 2021/0257849 A1 | 8/2021 | Keil et al. |
| 2021/0283409 A1 | 9/2021 | Keil et al. |

\* cited by examiner

OUTPUT CIRCUITRY FOR MULTIPLE-THERAPY IMPLANTABLE DEVICES

CROSS REFERENCE TO RELATED APPLICATIONS

This application claims the benefit of and priority to U.S. Provisional Patent Application Ser. No. 62/976,141 filed on Feb. 13, 2020, the disclosure of which is incorporated herein by reference.

BACKGROUND

Battery powered implantable devices, such as implantable defibrillators, may generate output stimuli having a larger voltage than the batteries of such devices can directly provide. Voltage boosting circuitry is typically used to create the higher voltages, including, for example, switched capacitor and/or transformer-based DC:DC conversion circuitry. In an implantable defibrillator, for example, a DC:DC circuit, such as a flyback transformer circuit, can be used to transfer power from a battery to a high power capacitor stack until the energy stored on the capacitor stack meets a therapy threshold. The stored energy is then discharged to the patient.

When discharging the energy, it is common to deliver therapy in a biphasic pattern that requires switching the direction of current flow. An H-Bridge circuit is often used to provide the switching capability. The switches of an H-Bridge, which may take the form of junction or field effect transistors, silicon controlled rectifiers, or other suitable circuitry, may be used in an ON/OFF manner, in which currents are not controlled, for delivering high power therapy such as defibrillation. It may be desirable in some instances to reuse this circuitry to provide controlled current outputs. New and alternative circuit designs and methods for providing controlled current outputs are desired.

Overview

The present inventors have recognized, among other things, that a problem to be solved is the need for new and/or alternative approaches to the design and implementation of therapy delivery circuitry for use in therapeutic medical devices.

A first illustrative and non-limiting example takes the form of an electronic circuit for generating at least first and second power outputs for electronic output of a medical device, the circuit comprising: a power source; a transformer having a primary winding and at least first and second secondary windings; a transformer control circuit controlling power supply to the primary winding of the transformer from the power source; a first therapy capacitor coupled to the first secondary winding and a second therapy capacitor coupled the second secondary winding; a first power tier control circuit coupling each of the first and second capacitors, in series, to a load; and a second power tier control circuit coupling only the second capacitor to the load.

Additionally or alternatively, the second power tier control circuit is configured to issue a constant current output. Additionally or alternatively, the first power tier control circuit is configured to provide a truncated exponential output.

A second illustrative, non-limiting example takes the form of an implantable medical device comprising at least first and second electrodes configured for delivering electrical therapy to a patient, an output control circuit coupled to the first and second electrodes, and the electronic circuit of the first illustrative, non-limiting example and variants thereon, wherein the output control circuit is configured to selectively couple the first and second power tier control circuits to at least the first and second electrodes.

Additionally or alternatively, the output control circuit comprises an H-bridge comprising a high side with at least first and second legs and a low side with at least first and second legs, and: the first power tier control circuit comprises a first switch coupling the first and second capacitors, in series, to the high side legs of the H-bridge; and the second power tier control circuit comprises a second switch coupling the second capacitor to the high side legs of the H-bridge.

Additionally or alternatively, the first switch is an IGBT, and the second switch is a latching switch, wherein the output control circuit further comprises first and second paths to ground from the low side legs of the H-bridge, in which the first path to ground comprises a third switch, and the second path to ground is comprises a resistor in series with a fourth switch, the implantable medical device further comprising a controller configured to control the first, second, third and fourth switches as follows: to deliver higher voltage therapy, the third switch is closed to provide a low impedance path to ground from the H-bridge, and the first switch is used to initiate and terminate therapy delivery; to deliver lower voltage therapy, to initiate therapy, the third switch is opened and the second and fourth switches are closed, with closing of the fourth switch and opening of the third switch providing a path to ground from the H-bridge through the resistor, and the fourth switch is opened to terminate therapy delivery.

Additionally or alternatively, each leg of the H-bridge uses a latching switch.

Additionally or alternatively, the output control circuit comprises an H-bridge having a high side with at least first and second legs and a low side with at least first and second legs, the H-bridge defining a first output node at a junction of the first high side leg and first low side leg, and a second output node at a junction of the second high side leg and the second low side leg, and: the first power tier control circuit comprises a first switch coupling the first and second capacitors, in series, to the high side legs of the H-bridge; and the second power tier control circuit comprises a second switch coupling and output thereof to first output node, and a third switch coupling the output thereof to the second output node.

A third illustrative, non-limiting example takes the form of an electronic circuit for generating at least first and second power tiers for electronic output of a medical device, the circuit comprising: a high voltage therapy subcircuit; a low voltage therapy subcircuit; an H-bridge comprising first and second high side legs and first and second low side legs, each leg comprising a switch, the first high side and first low side legs coupled together at a first load node, and the second high side and second low side legs coupled together at a second load node; wherein the high voltage therapy subcircuit is coupled to the first and second high side legs, and the low voltage therapy subcircuit is coupled to the first and second load nodes, thereby omitting the switches of the first and second high side legs of the H-bridge from a current path for the low voltage therapy subcircuit.

Additionally or alternatively, the switches in each leg of the H-bridge are latching switches. Additionally or alternatively, the high voltage therapy subcircuit comprises a non-latching enable switch having on and off states switchable between on and off states responsive to an input signal, and the low voltage therapy subcircuit comprises a latching enable switch.

Additionally or alternatively, the third illustrative, non-limiting example may further comprise first and second paths to ground from the low side legs of the H-bridge, the first path comprising a switch and the second path comprising a resistor in series with a switch, and a control circuit couples to the first and second paths, the H-bridge, and the high and low voltage therapy subcircuits, the control circuit configured to use the first path in conjunction with the high voltage therapy subcircuit, and the second path in conjunction with the low voltage therapy subcircuit.

Additionally or alternatively, the third illustrative, non-limiting example may further comprise first and second paths to ground from the low side legs of the H-bridge, the first path comprising one or more diodes in series, and second path comprising a resistor, a feedback circuit adapted to receive a feedback signal, and a controller configured to operate in a current controlled or non-current controlled manner by: in the current controlled mode, using a current indicating signal from the feedback circuit to control current; and in the non-current controlled mode, either ignoring the current indicating signal from the feedback circuit, or powering down one or more parts of the feedback circuit.

A fourth illustrative, non-limiting example takes the form of an electronic circuit for generating at least first and second power tiers for electronic output of a medical device, the circuit comprising: a high voltage therapy subcircuit; a low voltage therapy subcircuit; an H-bridge comprising first and second high side legs and first and second low side legs, each leg comprising a switch, the first high side and first low side legs coupled together at a first load node; and the second high side and second low side legs coupled together at a second load node; an H-bridge enable switch coupled to the first and second high side legs; wherein the high voltage therapy subcircuit is coupled to the H-bridge enable switch, and the low voltage therapy subcircuit is coupled to the first and second high side legs, thereby omitting the H-bridge enable circuit from a current path for the low voltage therapy subcircuit.

Additionally or alternatively, the fourth illustrative, non-limiting example may further comprise first and second paths to ground from the low side legs of the H-bridge, the first path comprising a switch and the second path comprising a resistor in series with a switch, and a control circuit couples to the first and second paths, the H-bridge, and the high and low voltage therapy subcircuits, the control circuit configured to use the first path in conjunction with the high voltage therapy subcircuit, and the second path in conjunction with the low voltage therapy subcircuit.

Additionally or alternatively, the fourth illustrative, non-limiting example may further comprise first and second paths to ground from the low side legs of the H-bridge, the first path comprising one or more diodes in series, and second path comprising a resistor, a feedback circuit adapted to receive a feedback signal, and a controller configured to operate in a current controlled or non-current controlled manner by: in the current controlled mode, using a current indicating signal from the feedback circuit to control current; and in the non-current controlled mode, either ignoring the current indicating signal from the feedback circuit, or powering down one or more parts of the feedback circuit.

Yet further illustrative, non-limiting examples take the form of an implantable, or non-implantable, medical device comprising at least first and second therapy delivery electrodes and an electronic circuit as the third or fourth illustrative, non-limiting examples, and/or variants thereon.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
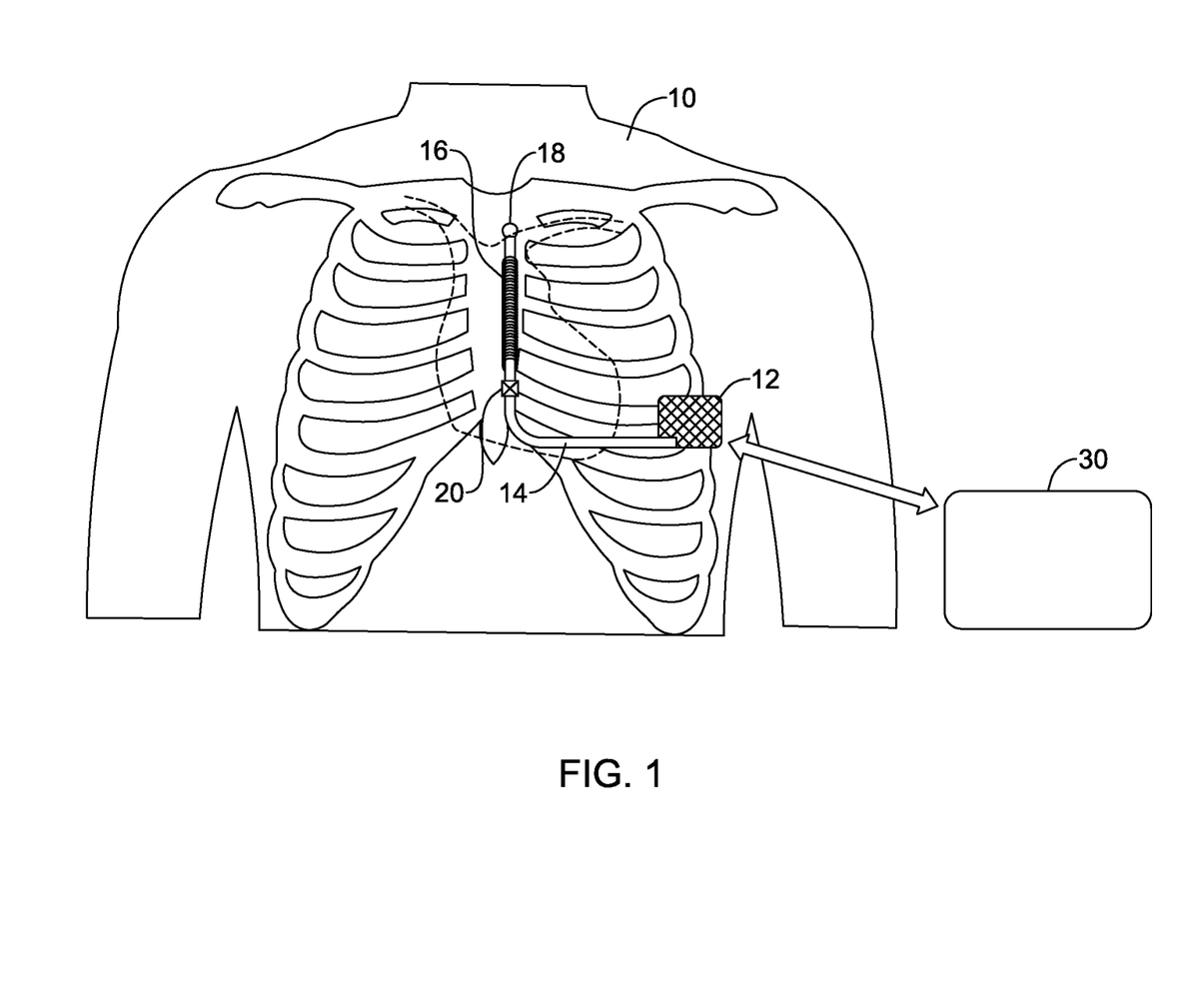
FIG. 1 shows an implantable stimulus system relative to the torso of a patient.

FIG. 1 shows an implantable stimulus system relative to the torso of a patient 10. In the example shown, an implantable canister 12 is placed near the left axilla, with a lead 14 extending medially therefrom. The lead 14 turns near the xiphoid to advance in a superior direction, toward the head generally parallel the sternum and over the heart. The lead 14 is shown illustratively as having a defibrillation coil electrode 16 and distal and proximal sense electrodes 18, 20. An external programmer 30 can wirelessly communicate with the canister 12 to provide therapy and sensing instructions to the system and to check various device status, history and diagnostic factors. The present invention is not limited to the specific lead 14 design shown, nor position of either the lead 14 or canister 12, and a variety of details and alternatives are disclosed in the patents and applications cited in the following paragraph, each of which may be used in various embodiments of the present invention.

The example of FIG. 1 shows the lead 14 placed over the ribs, in a subcutaneous position. Other subcutaneous positions may be used, such as described in US PG Pat. Pub. No. 20120029335, and U.S. Pat. Nos. 8,157,813, 7,149,575, 6,721,597, and 6,647,292, the disclosures of which are incorporated herein by reference. In other examples, the lead may be placed beneath the sternum in a substernal position, in the mediastinal space, as described in US PG Pat. Pub. No. 20170021159, and/or U.S. Pat. No. 10,471,267, the disclosure of which are incorporated herein by reference. In still other examples, the internal thoracic vasculature (including the internal thoracic vein or ITV) may be used for implantation as a final placement or as an avenue to the mediastinum, as described in US PG Pub. Nos. 20180133462, 20180036547, 20180036527, the disclosures of which are incorporated herein by reference. Such systems use sensing and therapy electrodes disposed in positions that neither contact nor enter the heart.

Approaches that use pacing electrodes that neither enter nor contact the cardiac tissue call for increased pacing amplitude when compared to transvenous, intracardiac or epicardial electrodes. Historically two separate output paths would be used for an implantable transvenous defibrillator having both pacing and defibrillation therapy capabilities, with a low voltage pacing therapy deliverable directly off of the battery stack or with a limited voltage boost, while a transformer-based circuit would be used to transfer power from the battery to a high voltage (HV) capacitor or capacitor stack for defibrillation purposes. However, with increased pacing amplitude needed for these newer, substernal, ITV, extracardiac or subcutaneous pacing configurations, the prior solutions become less usable. For example, with the SICD System™, three series batteries are used in the device, providing a nominal output voltage in the range of 9 to 9.5 volts, under light load; the pacing output of this system, used in the post-defibrillation shock context, delivers a 200 mA pacing output into a range of impedances from 25 to 200 ohms (assuming impedance measured during shock delivery), which means pacing can be delivered at up to 40 volts, more than four times the battery voltage. Pacing, when delivered, may be used for any of bradycardia support (chronic or post-defibrillation), as an anti-tachyarrhythmia pacing therapy, or for alleviation of heart failure systems, such as resynchronization therapy, without limitation.

Pacing is delivered at a relatively low duty cycle; a higher duty cycle, such as when inducing fibrillation for testing purposes (as is common at implant), can use a higher duty cycle, requiring still more DC:DC boosting capability. Induction testing is performed to demonstrate one or both of the sensing capability of an implanted system and its ability to convert ventricular fibrillation to a normal rhythm with therapeutic shock. In the realm of transvenous defibrillators, there is a trend away from universal induction testing. However, induction testing continues to be widely used, and in particular can be expected to be a continued practice with newer sub sternal, ITV, extracardiac and/or subcutaneous defibrillation systems.

Some proposals include adding a separate "pacing therapy" boost circuit and capacitor array to provide intermediate level power for pacing purposes. However, provision of multiple, separate circuits to provide the needed boosting increases complexity, cost, and space requirements, as well as complicating other factors such as reliability. A transformer-based circuit can be used to transfer very large amounts of power from a battery to a capacitor stack, and this technology is widely used in implantable defibrillators today to provide higher power cardioversion and/or defibrillation therapy outputs. Moreover, the commonly used output circuit for defibrillation therapy, which is called an H-bridge due to its shape, having first and second high side legs that meet at first and second load nodes with first and second low side legs, is already present in the device. New and better ways to facilitate multiple output levels, without overly complicating the apparatus, are desired.

While the development of the present invention may focus generally on some of the newer implant positions (subcutaneous, substernal, mediastinal or ITV), the present invention may also be used in more therapy systems with still older implantation positions, including epicardial or transvenous systems having leads and/or electrodes located in or on the heart. In addition, the present invention may also be used in wearable or external medical device systems, such as, but not limited to, wearable, automated external, and clinical/hospital defibrillators.

Figure 2:
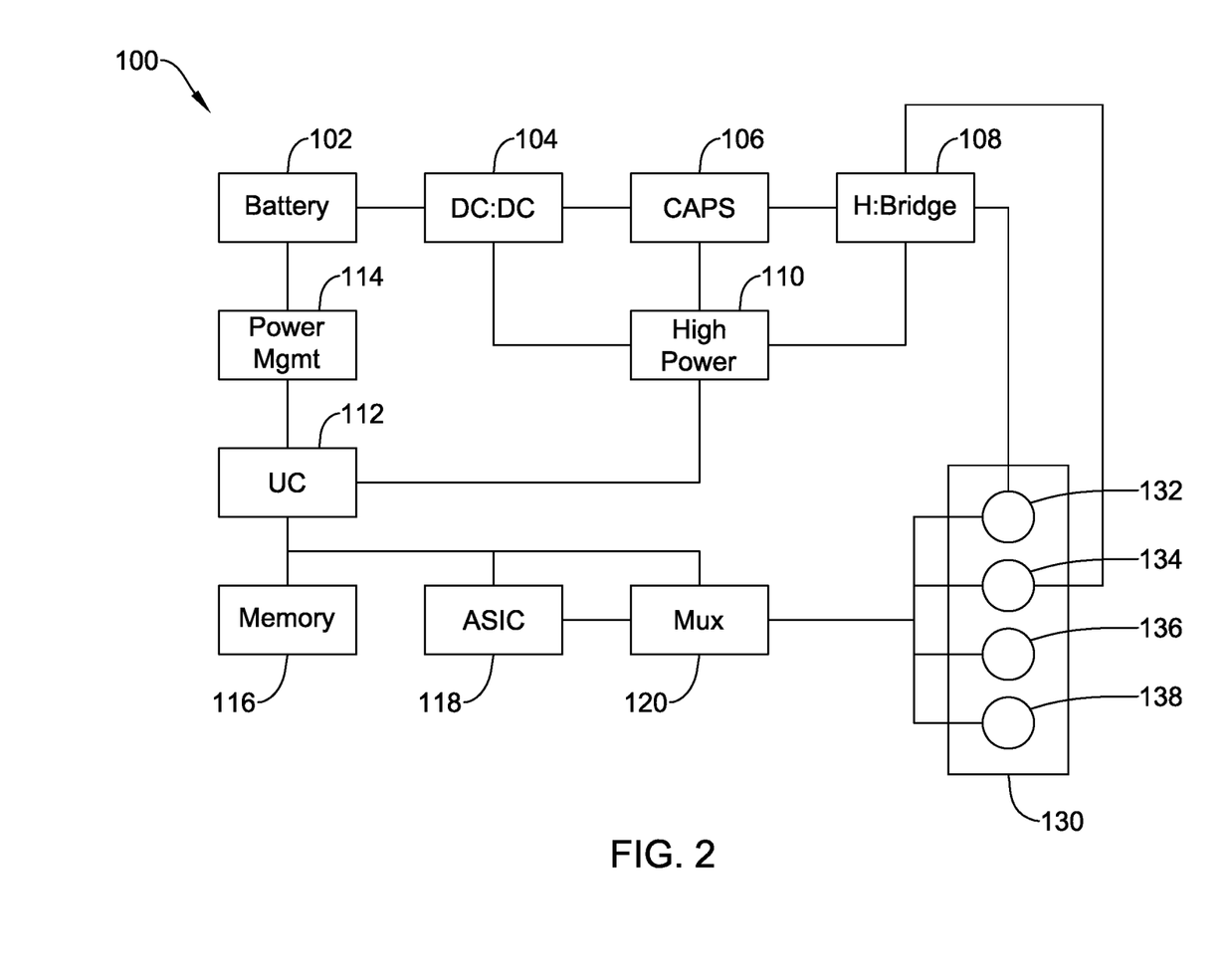
FIG. 2 shows an illustrative block diagram for an implantable stimulus system.

FIG. 2 shows an illustrative block diagram for an implantable stimulus system. The illustrative system 100 is powered by an internal battery 102, which may be of any suitable chemistry for an implantable medical device, such as any of various lithium chemistries (Lithium-Ion, LiMnO2, etc.). The battery 102 may comprise any suitable number of battery cells, such as 1, 2, 3, 4 or more cells. The battery 102 in the example is a non-rechargeable battery; in other examples a rechargeable battery may be used and, if so, a recharging circuit comprising, for example, an inductive coil that can be energized by an external coil may be used, such as described in U.S. Pat. No. 9,814,889 and/or as such systems are known for spinal cord stimulation such as in U.S. Pat. Nos. 8,548,590, 8,473,066 and/or 8,463,392, the disclosure of which are incorporated herein by reference.

The battery 102 can be used for high power therapy delivery by routing the battery output to a DC:DC converter 104 to charge a capacitor stack 106, with an H-Bridge used to issue therapy pulses via electrodes coupled to ports 132, 134. Optionally, in some examples, blocks 104, 106 and 108 reside on a high power hybrid (circuit board) 110 separate from lower power circuitry to reduce interference, among other benefits.

In some examples, a transformer is used as the DC:DC charging circuit, using a flyback transformer layout in which the battery output is directed to a primary coil of the transformer and one or more secondary coils each charge a capacitor of the capacitor stack 106. In operation, the charging sequence alternates between primary and secondary phases. During the primary phase, the transformer receives power from the battery 102, with current passing from the battery, through at least a switch and the transformer to ground. During the secondary phase, the switch is opened, causing an open circuit of the transformer primary coil, driving the energy stored in the transformer during the primary phase into the capacitor stack 106. Appropriately placed diodes can be used to manage current flow and ensure appropriate charging takes place. Switching between primary and secondary phases can be controlled via a timing schedule, or may occur in response to measured currents reaching upper or lower thresholds, or a combination of both, such as having a fixed interval primary phase and a current controlled secondary phase.

While several references herein are to a capacitor stack 106, having, for example, anywhere from 2-6 capacitors, or more, a single capacitor may be used if desired. The drawing indicates dedicated output or output ports 132, 134 which may be, for example, an output coupled to a conductive canister (or portion thereof) that contains the circuitry 100 and an electrode on a lead. In other examples, two lead electrodes, or two housing electrodes, or more than two electrodes may be used for therapy delivery; additional switching circuitry may be used to direct therapy outputs as desired.

In the illustrative example, lower power circuitry is (optionally) powered by a power management block 114 that provides regulated voltages off of the battery 102, such as, for example and without limitation, 1.8, 3.2, 5.1, or other voltages, which are typically reduced relative to the battery output to ensure stable voltages over the useful life of the device, during which the battery voltage typically degrades. Some examples may also include, for example, a 15 volt supply that can be generated by a switched capacitor voltage booster (assuming the battery 102 provides less than 15 volts). A plurality of such power supplies may be included to address various needs in the system, such as, for example and without limitation, providing a 5-volt supply to power a telemetry antenna while a 3.2 volt supply powers a microcontroller.

A microcontroller 112 may be provided for managing various device operations, with a memory 116 provided to store executable instructions as well as device history data, such as measured battery voltages and recorded cardiac data related to "episodes" in which therapy is delivered, as well as any other information or instructions used in the system. An application specific integrated circuit (ASIC) 118 is illustratively shown and, without intending to limit the invention any particular one of these items, may include circuits dedicated to particular tasks, such as an input ECG circuit that filters, amplifies and digitizes sensed signals. Other circuits on the ASIC may include dedicated beat detection circuitry, and/or dedicated morphology analysis circuitry such as a correlation analysis or wavelet comparison circuit. The ASIC 118 may comprise or be coupled to telemetry circuitry using, for example, Medradio, inductive telemetry, or Bluetooth (including Bluetooth Low Energy) communication circuitry. The power management block 114, or portions thereof, may be integrated into the ASIC 118 if desired. In some implementations, the ASIC is used to perform and/or manage ongoing operations of the system as the microcontroller is generally kept in a low power or sleep mode, and the ASIC can issue periodic or occasional signals to wake up the microcontroller as for example may occur when a new heartbeat occurs, or when a calculated heart rate crosses a high rate threshold, or a signal is received on telemetry circuitry indicating the initiation of a communication session, among other triggers for microcontroller wakeup.

A switching circuit is also shown as a multiplexor 120 for coupling to a plurality of inputs/outputs 130, shown as four input/output lines 132, 134, 136, 138; more or fewer input/output lines may be included. In some examples the switching circuitry is used to select one or more sensing vectors defined by pairs or groups of electrodes used for sensing purposes, such as disclosed, for example, in U.S. Pat. Nos. 8,825,157, 7,783,340, 8,200,341, and/or US PG Pat. Pub. Nos. 20170113053, 20170113050, 20170113040, and/or 20170112399, the disclosures of which are incorporated herein by reference.

Figure 3:
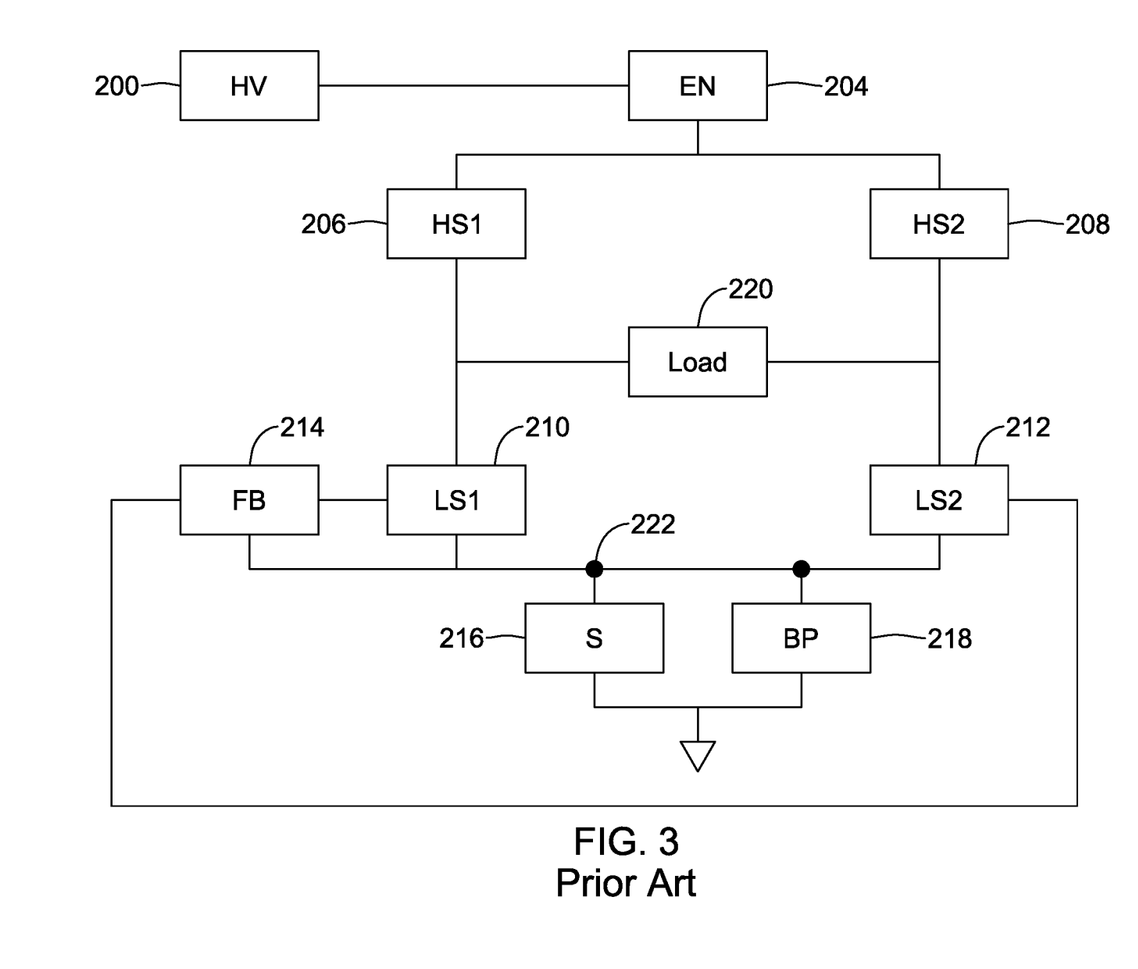
FIG. 3 shows a prior art output circuit.

FIG. 3 shows a prior art output circuit. The illustrative circuit delivers power from the HV Capacitors 200 to a load 220, which represents the patient. An enable switch 204 sit outside (above) the H-Bridge, which comprises two high side switches 206, 208 and two low side switches 210, 212. In this example, the low side switches 210, 212 can be used as ON/OFF switches during defibrillation, and can be used to control current during pacing and induction processes by the use of a feedback circuit 214. Between the H-Bridge and ground are a sense resistor 216 and a bypass switch 218.

To issue therapy, a combination of the enabling switch 204 and one high side and one low side switch are closed. In a first polarity output, switches 204, 206 and 212 are closed; to deliver output of the opposite polarity, switches 204, 208 and 210 are closed. During defibrillation therapy, the sense resistor 216 may be bypassed by closing the bypass switch 218, reducing the impedance within the circuit during defibrillation. Biphasic therapy can be issued by monitoring the HV Capacitors 200 to determine when a threshold voltage for switching polarity is reached, such as 40, 50, 60, or 70% (or other value) drop in voltage.

For controlled current pacing and induction purposes, the bypass switch 218 is opened, forcing current through the sense resistor 216. The feedback circuit 214 obtains a sense signal from the sensing node 222 and provides a controlled enabling voltage to one of the low side switches 210, 212 (depending on which polarity of output is active) to keep the voltage at node 222 fixed to a predetermined value. For example, when the voltage at node 222 is lower than a target value, that means less than a target current is flowing through sense resistor 216, so the voltage provided to enable whichever of switches 210, 212 is being operated is increased until the voltage at node 222 reaches the target value. To limit the amount of power that has to be absorbed by switches 210, 212, the HV Capacitors 200 are charged for pacing and induction to a voltage that is lower than that used for defibrillation, as, for example, by charging to a level that will enable current to reach the target value for the maximum allowable load impedance. For example, if the maximum allowable, or expected, load is 200 ohms and the current to be issued is 200 mA, then the HV Capacitors 200 may be charged to a value that exceeds 40 volts plus some margin to account for parasitic losses in the lines, losses due to the various transistors/switches used, and attenuation caused by the sense resistor 216. In contrast, peak defibrillation voltages may range, for example and without limitation, from 750 to 1500 volts, depending on system type and programming.

A drain circuit for the HV Capacitors 200 is omitted in the drawing, but may be understood as comprising one or two resistive branches. In a two-branch version, a passive drain branch having a large impedance (1 Mohm, for example) provides a slow drain on the HV capacitors to ensure that a large voltage is not held indefinitely, while a smaller resistor (10 kohm, for example) is provided in series with a switch to allow the HV Capacitors 200 to be drained to a reduced voltage if needed, for example, to allow pacing therapy output after a defibrillation shock if reduced HV Capacitor voltage is desired during pacing relative to the residual voltage after defibrillation shock. Another context for using an active drain branch may be if a patient undergoing induction testing spontaneously converts to normal rhythm while the HV Capacitors 200 are being charged, in which case is may be desirable to drain the HV Capacitors 200 prior to the next induction attempt.

A system controller is omitted in FIG. 3, as well as in several later figures that show an H-bridge layout and associated circuitry. It should be understood that a system control is present and provides supervision, monitoring, and/or direct control over the various elements shown via connections that are omitted to avoid unduly complicating the Figures. In some operations, both a system controller, such as a microcontroller, and an application In this circuit, because the low side switches 210, 212 are used to control current flow, they have to absorb a significant amount of power in the controlled current mode, and typically relatively large IGBT devices are used. Also in this circuit, the high side switches 206, 208, and the enable switch 204, are subject to a level shift during therapy output, as the load raises the emitter voltage on each to, practically speaking, the voltage on the HV Capacitors 200. Therefore an isolation circuit element, such as a transformer or optical isolator, is typically used to provide the control signal to each switch 204, 206, 208, reliant on a low voltage input. The use of isolation circuits may be reduced by, for example, using thyristors as switches 206, 208, if desired. The use of larger IGBT elements and the isolation elements increases cost and size of the circuit, and the isolation circuits may also add to the potential for quality issues, as optical isolators can be subject to thermal issues during manufacturing. Alternatives are desired.

FIGS. 4-8 illustrate new therapy and output circuit designs. Starting with FIG. 4, a power source 300 (shown as buffered with a capacitor) is used to drive the primary winding of a transformer 302 under control of a switch as part of the charger control circuit 310. The transformer 302 is used to transfer power, with voltage step-up, to a capacitor stack shown illustratively having first and second capacitors 304, 306.

Figure 4:
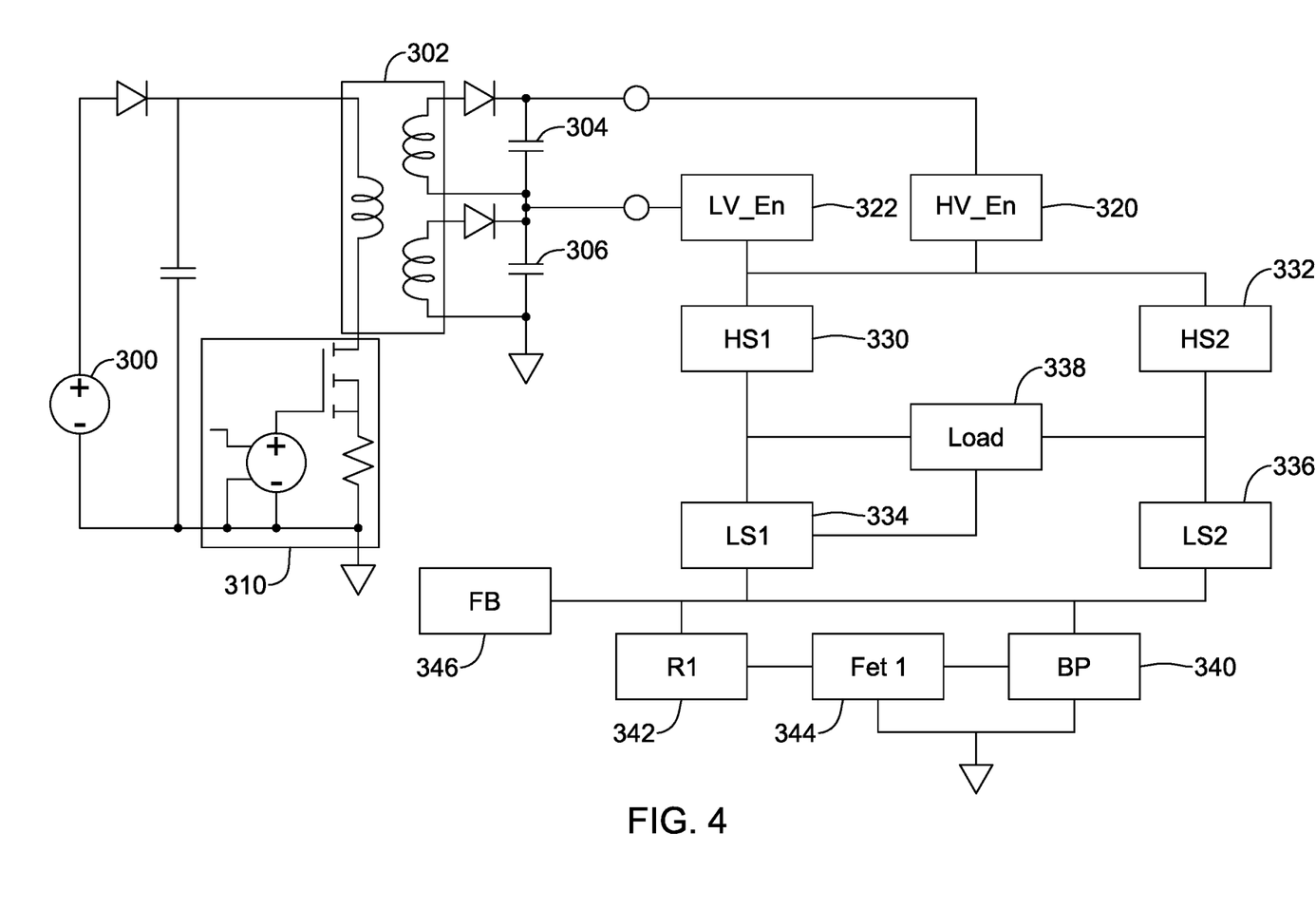
FIGS. 4-8 illustrate new output circuit designs.

The circuit includes two enabling sub-circuits to provide power to an H-bridge for therapy purposes. A first or high voltage (HV) enable subcircuit is shown at 320, and receives therapy energy from the two capacitors 304, 306 in series. A second or low voltage (LV) enable subcircuit 322 receives therapy energy from just the second capacitor 306 in the illustrative example. The use of two capacitors 304, 306 is merely illustrative and should not be considered limiting; more capacitors may be used in other examples.

The H-Bridge is shown with a standard layout including first and second high side switches 330, 332 and first and second low side switches 334, 336, thus defining first and second high side legs and first and second low side legs. Therapy can be routed to the load 338, which may be, for example, targeted patient tissue, by closing select switch pairs (330, 336 for current in one direction, and 332, 334 for current in the opposite direction). The low side switches 334, 336 are shown for illustrative purposes as coupled to a bypass switch 340, which can be used to deliver an output without current control by offering, when closed, a low impedance path to ground. Parallel to the bypass switch 340 is a controlled current line comprising a resistor 342 in series with a switch 344, with switch 344 shown as a simple field effect transistor (FET). When bypass switch 340 is open and switch 344 is closed, current through the H-Bridge routes through the resistor 342 to provide a feedback signal that can be monitored/measured by a feedback circuit 346. In this example, the feedback circuit 346 can be used to control the LV enable subcircuit 322 to control current flow into the H-Bridge. Switch 344 is optional and may be omitted, if desired, to simplify the setup; it may be included to protect the resistor 342 from high currents during defibrillation if desired.

In some examples, the sense resistor 342, with or without the FET 344, may be described as a current monitoring subcircuit. A current monitoring subcircuit may further comprise, for example, a comparator or an analog-to-digital convertor. A comparator may be used, for example, to compare the voltage across the sense resistor 342, to a predetermined voltage, or a controllable voltage, and provides an indication of whether the voltage through the sense resistor (which is directly proportional to the current therethrough) is above or below a target or threshold that the predetermined or controllable voltage is indicative of. An analog to digital convertor, if used, provides a measurement output in digital form telling the system controller what voltage has been measured; again, the voltage through the sense resistor would be directly proportional to the current, and knowing the resistance value of the sense resistor, simple division allows the current to be calculated. Thus, for example and without limitation, if a comparator is used, and a 50 ohm resistor is used as sense resistor 342, to obtain a 100 milliamp current, the predetermined or controllable voltage may be 5 volts. In another example, an inductive current measuring apparatus is placed in series with the H-Bridge, using, for example, a Hall effect device or flux gate sensor to sense current flow, with or without a bypass switch 340. This combination of items 340, 342, 344 may be used in any of the examples herein to provide selectable current sensing/control, as desired.

It should be understood that an H-bridge, as that term is used, may have more than two high and/or low side legs to allow the use of more than one output vector, if desired. References herein to first and second high and/or low side legs of an H-bridge should be understood as not limiting to just two such legs.

Figure 5:
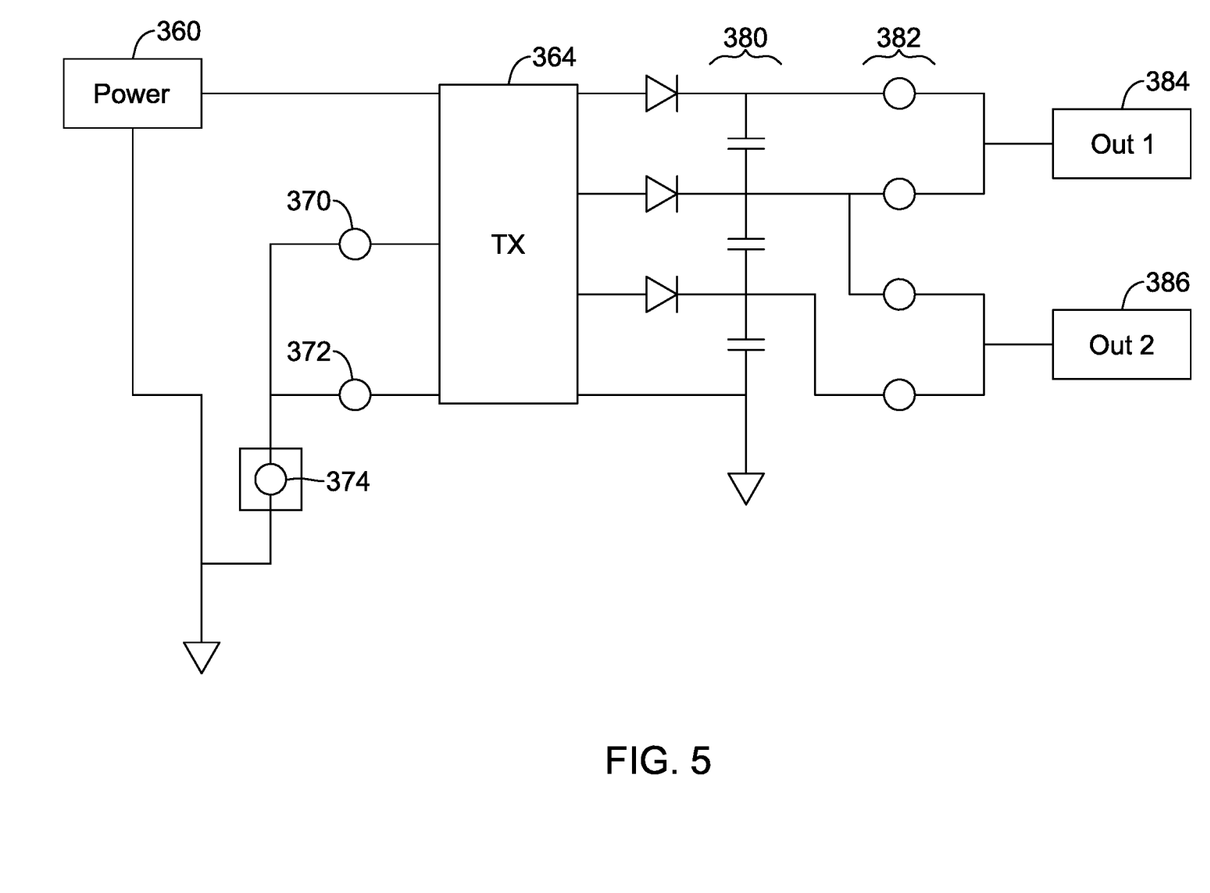

FIG. 5 shows another example directed at the use of the transformer and capacitor stacks with additional flexibility. The power source 360 here is coupled to a transformer 364 having a multi-tap primary coil as well as a multi-coil secondary. Which tap of the primary coil is used is controlled by switches 370, 372, while activation and deactivation of the primary coil overall is controlled with a charger control circuit 374. For example, switch 370 may couple to a primary winding tap, such as a center tap (or any other position in the winding), while switch 372 couples to the entire primary winding resulting in a different turns ratio for the transformer 364 depending on which of switch 370 or 372 is closed when the charger control circuit 374 is activated.

For added flexibility, the transformer 364 here may include, for example, three secondary windings, providing three output pins and a ground pin on the secondary side of the transformer 364. The three secondary winding are diode coupled to a capacitors stack at 380, shown as having three capacitors each corresponding to a secondary winding. A switch array at 382 allows selective coupling of all or less than all of the capacitors through a first output 384, and a different subset of the capacitor stack to a second output 386. For example, two or three of the capacitors 380 may be used to provide the first output 384, while one or two of the capacitors 380 may be used to provide the second output 386.

It should be noted that the example in FIG. 5 includes both primary side flexibility by offering at least two tap locations (more than two may be provided in other examples), and secondary side flexibility by allowing selection of different combinations of capacitors for each output 384, 386. In other examples, only the primary side flexibility is offered, or only the secondary side flexibility is offered. If desired, additional switching circuitry may appear between the transformer 364 and the capacitor stack 380, to allow more or fewer of the secondary taps to be routed to one or more of the capacitors.

Figure 6:
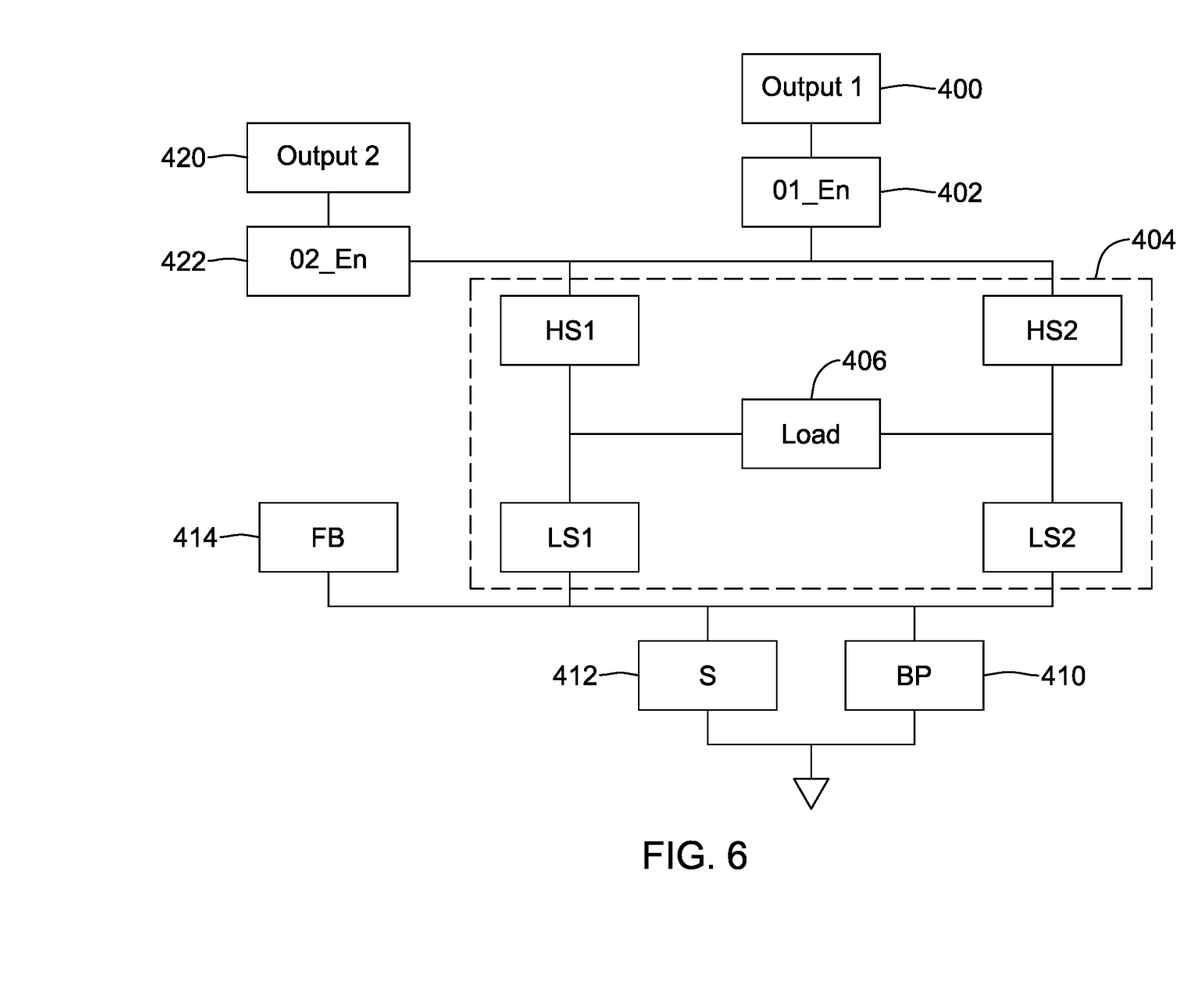

FIG. 6 shows another example. Here, a first output circuit 400 is selectably provided via a first output enable switch 402 to the H-bridge 404, which in turn configurably provides the signal to the load 406. Additionally, a second output circuit 400 is selectably provided via a second output enable switch 422 to the H-bridge 404, which again configurably provides the signal to the load 406.

For example, the first output circuit 400 may comprise a charger and capacitor stack to offer a first therapy amplitude or amplitude range for an output, while the second output circuit 420 may include a constant current output, such as may be generated by use of a current mirror architecture (see, for example, U.S. Pat. No. 8,620,436, the disclosure of which is incorporated herein by reference). A constant voltage may be provided instead, such as by using a digital-to-analog convertor with a buffer or amplifier coupled thereto. Reverse protection diodes may be used for such a system to provide added protection to the lower power set of circuits; for example, adding one or more diodes in series with the second output enable switch 422 may provide protection to the second output circuit 420 when high power outputs are generated by the first output circuit 400. When used in this manner, at least three different power tiers may be enabled:

A first power tier can be one in which the first therapy circuit 400 is a capacitor or capacitor stack charged to a defibrillation energy level (30 or more Joules, for example), with the bypass switch 410 closed during therapy delivery and each switch in the H-bridge, as well as the first therapy enable switch 402 used in an ON/OFF manner.

A second power tier can be one in which the first therapy circuit 400 is still a capacitor or capacitor stack, but now charged to a lower energy level to support induction or pacing, for example, with the bypass switch 410 open to route current from the H-bridge to ground through a sensing circuit 412, providing feedback 414 that can be used to control current by manipulation of the first enable circuit 402 and/or one of the switches in the H-Bridge, which may be an IGBT used in a current controlling mode.

A third power tier can be one in which a still more closely controlled output current or voltage is generated by the second output circuit 420 for use in any of various functions, such as to provide a conducted current communication signal (allowing an implanted device to communicate without the use of inductive or radiated fields as, for example, to communicate to a second implanted device through patient tissue) or an impedance testing signal. When using the third power tier, the bypass switch 410 may be either open or closed, since the generating circuitry provides sufficient control to the output and does not necessarily need the feedback signal 414. It may be necessary for the third power tier to consider maintaining an amplitude sufficient to allow each of the H-bridge switches 404 to remain closed, as some latching-type switches (Triac device and/or silicon controlled rectifier (SCR), for example) require at least a minimum current load to remain closed.

In another example, the first and second output circuits 400, 420 may comprise sets or subsets of a capacitor stack used in a manner similar to that described for FIG. 4, above. The example in FIG. 6 may be viewed as a general case of the approach shown in FIG. 4, to some extent. With this example, the output circuits 400 and 420 may be characterized as therapy circuits.

Another alternative configuration of the circuit in FIG. 6 may include the use of one or more diodes in place of the bypass switch, making block 410 a bypass circuit. A forward biased diode/rectifier, or reverse biased Zener diode, may be used in place of a switch at 410, as long as the sense resistor in 412 has sufficient current carrying capacity to accommodate however much current would flow during defibrillation due to the forward voltage of the diode/rectifier (or reverse breakdown voltage if a Zener diode is used). Thus, for example, if the feedback circuit 414 is configured to sense a voltage of 3 volts or less, a diode having a forward voltage greater than 3 volts (or two or more diodes in series) may be used instead of a bypass switch at 410, simplifying the control setup. Thus, for example, the feedback circuit 414 may include analog-to-digital convertor having a dynamic range that is less than the forward bias of the one or more diodes used in the bypass circuit 410. In another example, the bypass circuit 410 may use a reverse biased Zener diode, and the feedback circuit 414 may include analog-to-digital convertor having a dynamic range that is less than the reverse breakdown voltage of the Zener diode. In still other examples, the feedback circuit 414 may be configured to sense the feedback signal when the system is using a current controlled output mode, and to generate a current controlling signal therefrom. Such as signal may be compared to a threshold to determine if the current is above or below a target, or, in the alternative, may itself indicate whether the current is above or below a target that the feedback circuit itself analyzes. In such examples, to perform a non-current controlled output, the system may either not sense (by disabling or powering down an ADC or amplifier, for example or to sense but generally ignore the current controlling signal from the feedback circuit when performing, for example and without limitation, a voltage controlled defibrillation therapy.

Figure 7:
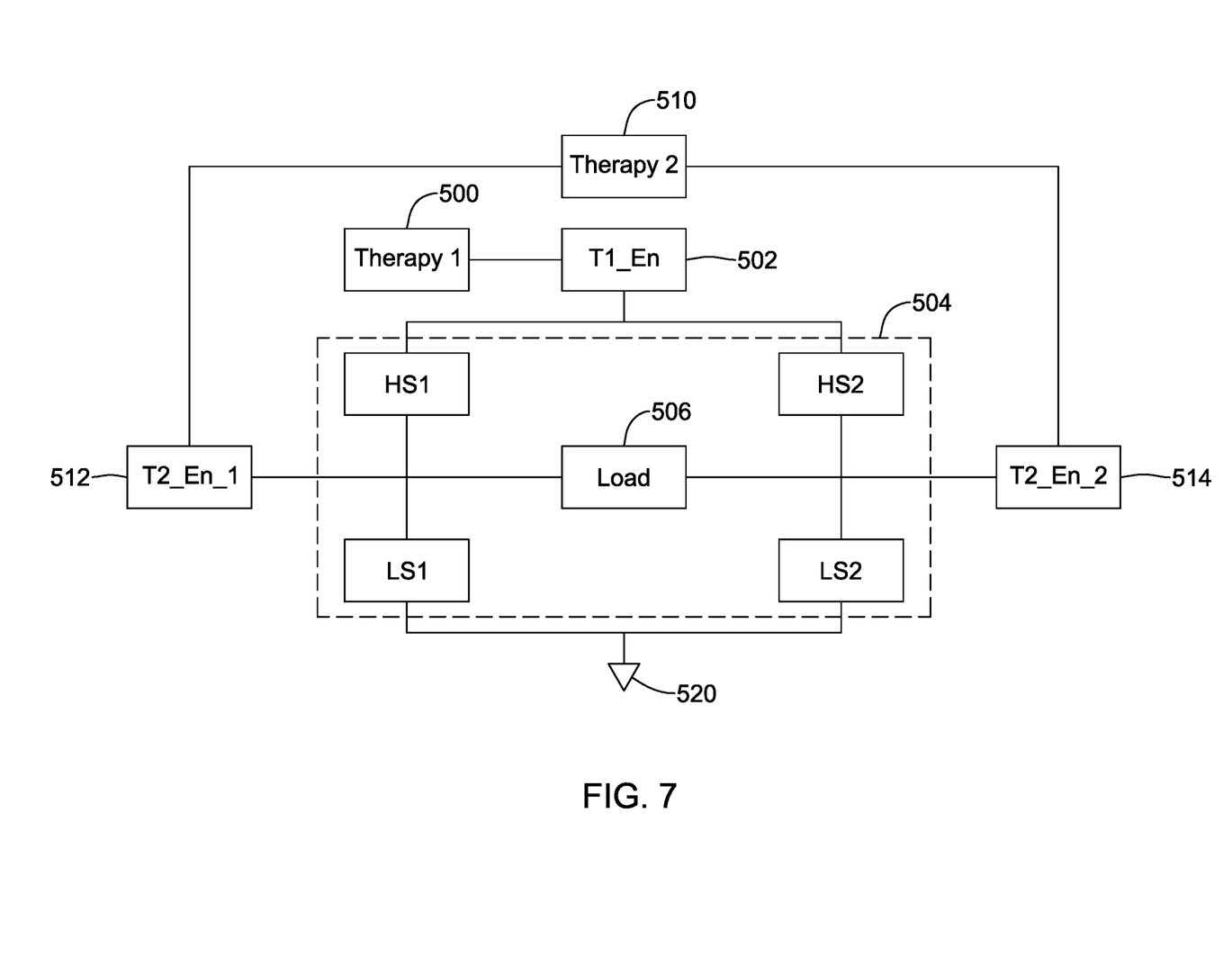

FIG. 7 shows another example. Here, a first therapy generation circuit 500 is coupled via a first therapy enable switch 502 to the H-bridge 504, which in turn routes signals to the load 506. The H-bridge defines a first node A between the first high side switch HS1 and the first low side switch LS1, and a second node B between the second high side switch HS2 and the second low side switch LS2. A second therapy generation circuit 510 is coupled by first and second enable switches 512, 514 to nodes A and B, respectively. Therapy from the second therapy generation circuit 510 can be routed through the load 506 by, for example, closing switch 512 and LS2 at the same time, or by closing switch 516 and LS1 at the same time, and thus does not route the output through either high side switch HS1, HS2 of the H-bridge 504. By this approach, minimum current requirements of the high side switches HS1 and HS2 do not need to be met by any therapy delivered from the second therapy generation circuit 510.

Optionally, as shown in FIG. 7, the H-bridge may simply be routed to ground as shown at 520. If desired, a shut-off switch may be provided between the H-bridge and ground to aid in truncating any delivered therapy, allowing the other switches in the H-bridge and one or more of the enable switches 502, 512, 514 to be simple ON/OFF switches. In another example, the enable switches 502 and 512/514 may be switches that do not latch to an on state, such as IGBT, while the switches in the H-bridge 504 are switches that do latch on, such as SCR or Triac devices. In other examples, the combination of bypass switch and resistor/sense enable switches shown, for example, in FIG. 6 may be added at 520, if desired.

Figure 8:
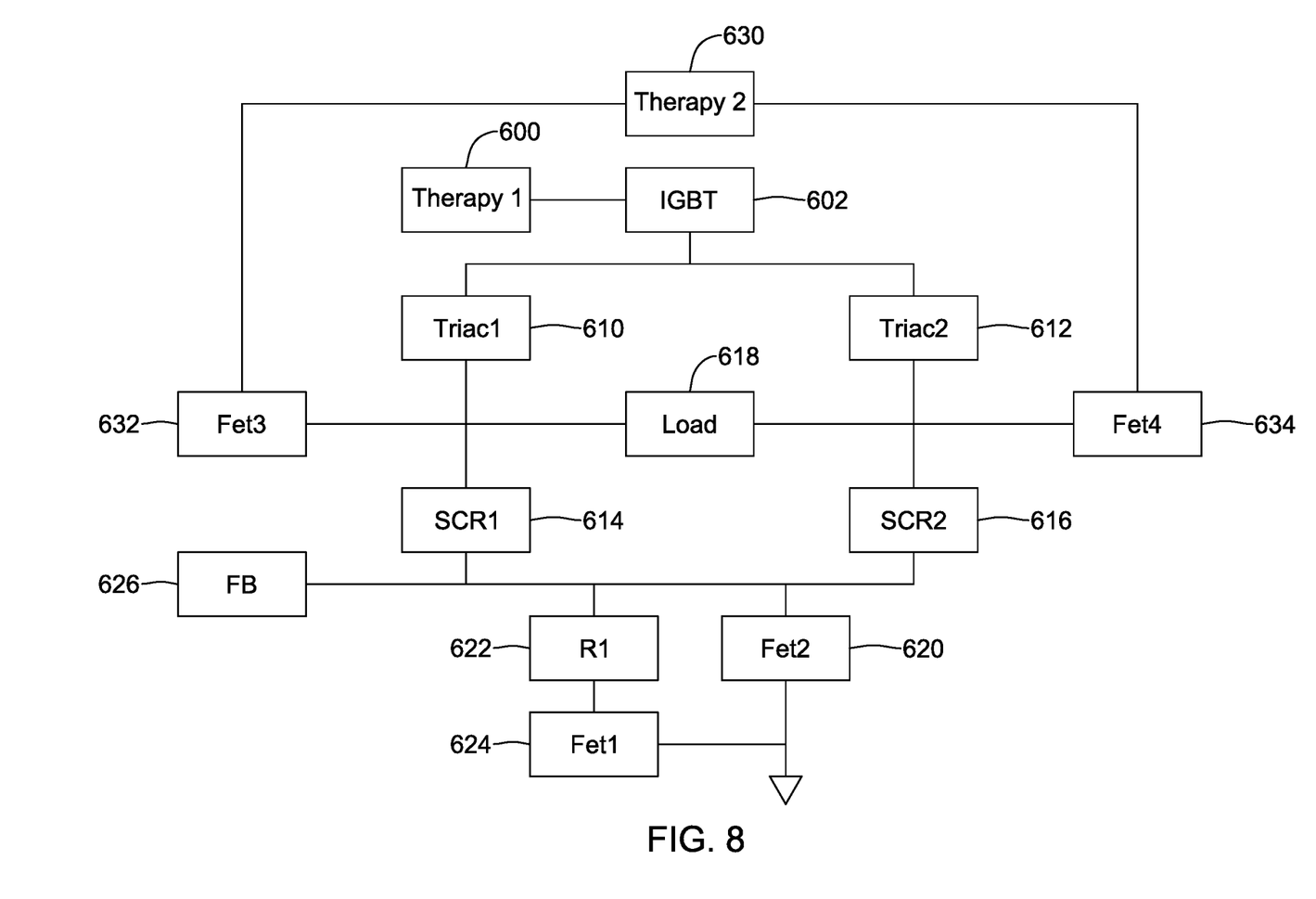

FIG. 8 shows another example similar to FIG. 7, this time with designation of select devices throughout the circuit, thus showing a particular, but non-limiting, implementation. A first therapy circuit 600 is coupled by an IGBT 602 to an H-Bridge. The H-bridge includes high side switches, implemented as Triac devices at 610, 612, and low side switches, implemented as silicon controlled rectifiers, at 614, 616, which meet at nodes on defining first and second polarities relative to a load 618.

In select examples, the load 618 may be, for example, an output of the system that can be coupled to patient tissue, such as a canister for an implanted device and an electrically conductive lead and defibrillation electrodes which may be, though is not limited to, a coil electrode carried on a lead. Other examples may use two lead electrodes, and omit a canister, while still other examples may use more than two electrodes for therapy delivery.

The bottom of the H-bridge is coupled, in this example, to two ground paths. A first ground path is defined by a switch, implemented as a simple field effect transistor (FET), such as a Mosfet, as shown at 620. Switch 620 may serve as a bypass switch to the second ground path, which uses a resistor 622 in series with another switch 624, again implemented as a FET. As discussed in other examples, the second path to ground, which is optional, can be used to generate a feedback signal when switch 620 is open and switch 624 is closed, providing a signal usable by a feedback circuit 626 to assist in any of various functions, including current control as well as current measurement, which may be useful, for example, to determine lead or tissue impedance.

A second therapy circuit 630 is also coupled to the H-Bridge using switch 632 and switch 634, with these switches 632, 634 shown as FET devices again. As with FIG. 7, the implementation in FIG. 8 allows the high side switches of the H-Bridge 610, 612 to be bypassed in this implementation.

Throughout the circuits shown in any of FIGS. 4-8 there may be additional connections and features that are omitted, including, for example and without limitation, additional connections to an ASIC or microcontroller used to supervise operations of the device. Also, a number of suitable reverse protection diodes may be included in the circuitry, such as in series with switches that couple lower voltage therapy or output circuits to higher power portions of the circuit including, for example and without limitation, in series with any of 320, 322 in FIG. 4, 402, 422 in FIG. 6, 502, 512, HS1 and HS2 in FIG. 7, and/or 602, 610, 612, 632, and/or 634 in FIG. 8. Reverse protection diodes may also be used in association with any of the low side legs of any of the H-bridge circuit shown.

Therapy decision making may include any of a variety of algorithms known in the art. In general, referring back to FIG. 2, the microcontroller 112 and associated memory and ASIC components may be adapted to receive electrical signals from the electrodes which are amplified and filtered to provide an input ECG signal. The input ECG signal can be compared to a time-varying threshold to detect heart beats, such as by detecting R-waves or QRS complexes in the cardiac signal. Such detections can be confirmed by analyzing for double detection and noise using known methods. The time elapsing between detected heart beats is recorded in order to calculate cardiac rate, which can be categorized suitable for a given system. For example, a pacemaker defibrillator may have a timeout period applied to detect long pauses between beats, indicating pacing should be delivered for bradycardia conditions. An adaptive pacemaker may use an input from, for example, a temperature sensor or motion detector, to adjust the timeout period to account for patient activity, allowing the paced heart rate to increase or decrease depending on patient activity. A defibrillator or tachyarrhythmia therapy system may also classify ventricular tachyarrhythmia (VT) and ventricular fibrillation (VF) rates, such as considering rates between 180 and 220 beats per minute (BPM) as VT, and rates above 220 BPM as VF (other rate threshold may be used, and the thresholds may be configurable by a physician or at a physician's request/order). VT rates may be used to trigger ATP, for systems that provide ATP and in which ATP is enabled. VF rates may trigger additional analysis for shock delivery, such as using an X/Y counter to determine how many beats (X) of a set of Y beats are deemed to indicate VF using, for example, shape analysis (morphology). Illustrative shape analysis techniques can include the use of correlation waveform analysis, in which a stored template of a "normal" beat electrical signature is compared to detected beats; low correlation may be deemed indicative of VF; detected beats may be compared one to another as well to differentiate VT from VF and/or to differentiate sinus tachycardia (resulting from exercise, for example) from VT and VF. Wavelet transformation analysis may also be used to analyze shape, as well as the width of beats. When VF is identified, preparations for defibrillation therapy can be commenced, including charging the capacitor stack to a defibrillation energy level (typically 30 Joules or more, and higher still if a subcutaneous-only system is used, where 60 Joules or more may be used).

In an example, a beat detection routine may be as described in U.S. Pat. No. 8,565,878, with cardiac signal analysis for overdetection performed as in U.S. Pat. No. 8,160,686. Arrhythmia discrimination may be performed using methods described in U.S. Pat. Nos. 6,754,528 and/or 7,330,757. With beats analyzed for arrhythmia, the overall rhythm may be assessed using methods as in US Patent Application Pub. No. 2006/01467503, and defibrillation therapy can be delivered when all requirements for defibrillation therapy have been met, meaning that sufficient arrhythmic beats are detected in a persistent manner allowing positive confirmation of treatable arrhythmia. The disclosures of each of these patents and patent applications are incorporated herein by reference for at least the purposes identified for each. However, other methods may be used at each step, if desired, and the invention is not limited to use with these particular algorithms.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An electronic circuit for generating at least first and second power outputs for electronic output of a medical device, the circuit comprising:
   a power source;
   a transformer having a primary winding and at least first and second secondary windings;
   a transformer control circuit controlling power supply to the primary winding of the transformer from the power source;
   a first therapy capacitor coupled to the first secondary winding and a second therapy capacitor coupled the second secondary winding;
   a first power tier control circuit coupling each of the first and second capacitors, in series, to a load; and
   a second power tier control circuit coupling only the second capacitor to the load.

2. The electronic circuit of claim 1 wherein the second power tier control circuit is configured to issue a constant current output.

3. The electronic circuit of claim 2 wherein the first power tier control circuit is configured to provide a truncated exponential output.

4. The electronic circuit of claim 1 wherein the first power tier control circuit is configured to provide a truncated exponential output.

5. An implantable medical device comprising at least first and second electrodes configured for delivering electrical therapy to a patient, an output circuit coupled to the first and second electrodes, and the electronic circuit of claim 1, the output control circuit configured to selectively couple the first and second power tier control circuits to at least the first and second electrodes, the output control circuit comprising an H-bridge further comprised of a high side with at least first and second legs and a low side with at least first and second legs.

6. The implantable medical device of claim 5 wherein
   the first power tier control circuit comprises a first switch coupling the first and second capacitors, in series, to the high side legs of the H-bridge; and
   the second power tier control circuit comprises a second switch coupling the second capacitor to the high side legs of the H-bridge.

7. The implantable medical device of claim 6 wherein the first switch is an IGBT, and the second switch is a latching switch, wherein the output control circuit further comprises first and second paths to ground from the low side legs of the H-bridge, in which the first path to ground comprises a third switch, and the second path to ground is comprises a resistor in series with a fourth switch, the implantable medical device further comprising a controller configured to control the first, second, third and fourth switches as follows:
   to deliver higher voltage therapy, the third switch is closed to provide a low impedance path to ground from the H-bridge, and the first switch is used to initiate and terminate therapy delivery;
   to deliver lower voltage therapy, to initiate therapy, the third switch is opened and the second and fourth switches are closed, with closing of the fourth switch and opening of the third switch providing a path to ground from the H-bridge through the resistor, and the fourth switch is opened to terminate therapy delivery.

8. The implantable medical device of claim 5 wherein each leg of the H-bridge comprises a latching switch.

9. The implantable medical device of claim 5 wherein the output control circuit comprises an H-bridge having a high side with at least first and second legs and a low side with at least first and second legs, the H-bridge defining a first output node at a junction of the first high side leg and first low side leg, and a second output node at a junction of the second high side leg and the second low side leg, and:
   the first power tier control circuit comprises a first switch coupling the first and second capacitors, in series, to the high side legs of the H-bridge; and
   the second power tier control circuit comprises a second switch coupling and output thereof to first output node, and a third switch coupling the output thereof to the second output node.

* * * * *